United States Patent
Galdonik et al.

[11] Patent Number: 6,010,464
[45] Date of Patent: Jan. 4, 2000

[54] CONTROLLED GUIDE WIRE RESISTANCE WASHER FOR GUIDE CATHETER EXCHANGE DEVICE

[75] Inventors: Jason A. Galdonik, Minneapolis; Todd A. Berg, Lino Lakes; Brian Scovil, Champlin, all of Minn.

[73] Assignee: SciMed Life Systems, Inc., Maple Grove, Minn.

[21] Appl. No.: 09/002,366

[22] Filed: Jan. 2, 1998

[51] Int. Cl.[7] .................................................. A61B 5/00
[52] U.S. Cl. ......................................................... 600/585
[58] Field of Search ................................. 600/434, 435, 600/585; 604/95, 167

[56] References Cited

U.S. PATENT DOCUMENTS

| | | | |
|---|---|---|---|
| 4,616,648 | 10/1986 | Simpson | 128/303 R |
| 4,824,435 | 4/1989 | Giesy et al. | 604/49 |
| 4,829,999 | 5/1989 | Auth | 128/303 R |
| 4,860,742 | 8/1989 | Park et al. | 128/303 R |
| 4,886,067 | 12/1989 | Palermo | 128/657 |
| 4,927,413 | 5/1990 | Hess | 604/95 |
| 4,928,693 | 5/1990 | Goodin et al. | 128/637 |
| 4,932,413 | 6/1990 | Shockey et al. | 128/657 |
| 4,944,740 | 7/1990 | Buchbinder et al. | 606/194 |
| 4,947,864 | 8/1990 | Shockey et al. | 128/772 |
| 4,976,689 | 12/1990 | Buchbinder et al. | 604/95 |
| 5,035,686 | 7/1991 | Crittenden et al. | 604/96 |
| 5,120,323 | 6/1992 | Shockey et al. | 604/282 |
| 5,131,407 | 7/1992 | Ischinger et al. | 128/772 |
| 5,147,377 | 9/1992 | Sahota | 606/194 |
| 5,195,535 | 3/1993 | Shank | 128/772 |
| 5,234,407 | 8/1993 | Tierstein et al. | 604/53 |
| 5,246,009 | 9/1993 | Adams | 128/772 |
| 5,255,690 | 10/1993 | Keith et al. | 128/772 |
| 5,263,932 | 11/1993 | Jang | 604/96 |
| 5,267,958 | 12/1993 | Buchbinder et al. | 604/96 |
| 5,269,759 | 12/1993 | Hernandez et al. | 604/96 |
| 5,281,203 | 1/1994 | Ressemann | 604/164 |
| 5,282,478 | 2/1994 | Fleischhaker, Jr. et al. | 128/772 |
| 5,300,085 | 4/1994 | Yock | 606/191 |
| 5,318,527 | 6/1994 | Hyde et al. | 600/585 |
| 5,325,746 | 7/1994 | Anderson | 81/487 |
| 5,336,184 | 8/1994 | Teirstein | 604/102 |
| 5,342,297 | 8/1994 | Jang | 604/53 |
| 5,345,937 | 9/1994 | Middleman et al. | 128/657 |
| 5,354,282 | 10/1994 | Bierman | 604/180 |
| 5,368,567 | 11/1994 | Lee | 604/102 |
| 5,376,074 | 12/1994 | Buchbinder et al. | 604/96 |
| 5,388,590 | 2/1995 | Horrigan et al. | 128/772 |
| 5,395,332 | 3/1995 | Ressemann et al. | 604/96 |
| 5,413,560 | 5/1995 | Solar | 604/164 |
| 5,415,639 | 5/1995 | VandenEinde et al. | 604/283 |
| 5,425,711 | 6/1995 | Ressemann et al. | 604/96 |
| 5,449,362 | 9/1995 | Chaisson et al. | 606/108 |
| 5,558,635 | 9/1996 | Cannon | 604/49 |
| 5,588,442 | 12/1996 | Scovil et al. | 128/772 |

FOREIGN PATENT DOCUMENTS 9 574 542 B1   5/1997   European Pat. Off. .

*Primary Examiner*—Max Hindenburg
*Attorney, Agent, or Firm*—Crompton, Seager & Tufte, LLC

[57] ABSTRACT

A device and method for exchanging guide catheters over a guide wire, while maintaining the position of the guide wire within a patient. One guide catheter exchange device includes an elongate shaft and a distally tapering tube disposed at the distal end of the shaft. The tube includes a guide wire lumen and a controlled resistance washer having an aperture disposed in line with the guide wire lumen. One controlled resistance washer is formed of a resilient material and has an aperture with a central hole and four radial slits. The radial slits form control flaps which have, in a relaxed state, a minimum inside dimension less than the outside diameter of the guide wire to be received. While receiving a guide wire, the control flaps are in a flexed state and exert a static frictional force on the guide wire. The exerted frictional force inhibits longitudinal movement of the guide wire. Guide wire movement could otherwise be result from frictional forces caused by proximally retracting the guide catheter over the guide wire.

16 Claims, 2 Drawing Sheets

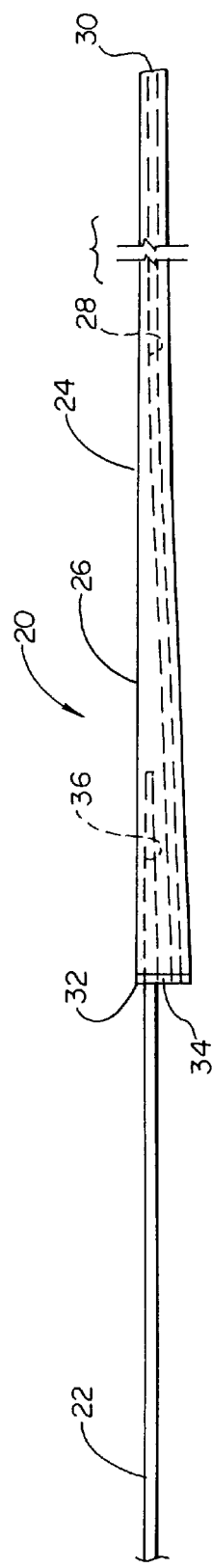
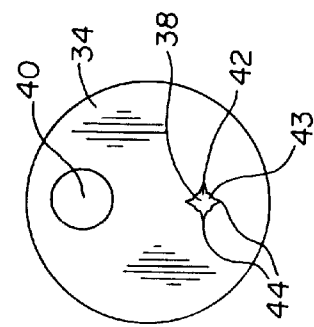
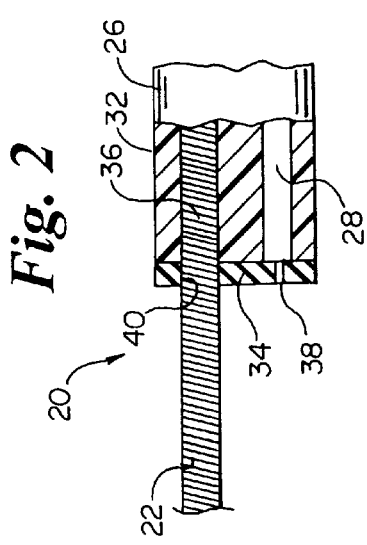

CONTROLLED GUIDE WIRE RESISTANCE WASHER FOR GUIDE CATHETER EXCHANGE DEVICE

FIELD OF THE INVENTION

The present invention is generally related to medical guide catheter and guide wires. More specifically, the present invention is related to a device and method for exchanging intravascular guide catheters over guide wires without dislodging the guide wire.

BACKGROUND OF THE INVENTION

Percutaneous transluminal angioplasty (PTCA) procedures are commonly used to treat stenotic lesions of the coronary arteries. PTCA procedures generally require the placement of an elongate flexible catheter known as a "guide catheter". The guide catheter is initially inserted through an entry site such as an incision in the femoral artery near the groin. The guide catheter is advanced over the aorta and can be further advanced into a coronary artery until the guide catheter distal end is near the targeted site. A flexible guide wire is then advanced through the guide catheter and the distal end of the guide wire is further advanced, exiting the guide catheter distally. The guide wire distal end is advanced, often with a degree of difficulty, until the distal end is across a stenotic region to be treated.

A balloon catheter is then advanced over the guide wire, within the guide catheter, exiting the guide catheter distally and approaching the stenosis. The balloon catheter can then be inflated and deflated repeatedly, until the desired dilation of the obstruction is accomplished. The guide wire, guide catheter and balloon catheter can then be withdrawn.

It is sometimes necessary to replace the initially selected guide catheter with a different guide catheter. This replacement may be required after the guide wire has been put into position across the stenosis and within the initial guide catheter. As the correct placement of the guide wire can be very difficult and time consuming, it is of great importance to maintain the position of the in-position guide wire. Retracting the guide catheter over the guide wire within can bring frictional forces to bear upon the guide wire. While the frictional forces over a small length of guide wire may not be great, the guide catheter can apply frictional force over much of its length. The frictional force can act to retract the guide wire from the desired position. Similarly, when the new guide catheter is being advanced over the guide wire, frictional forces can act to advance the guide wire distally past the desired position.

What would be desirable is a device for maintaining the position of a guide wire within a patient while a guide catheter is being retracted over the guide wire. What would be desirable is a device for maintaining the position of a guide wire within a patient while a guide catheter is being advanced over the guide wire.

SUMMARY OF THE INVENTION

The present invention provides a device for assisting in the exchange of a guide catheter. The device inhibits longitudinal movement of a guide wire extending through a guide catheter which is being retracted and can prevent the guide wire from becoming dislodged from its desired position during the guide catheter exchange. The guide catheter exchange device includes an elongate shaft member and means disposed distally on the shaft for receiving a guide wire and providing resistance to longitudinal movement of the guide wire.

In one embodiment, the means for receiving the guide wire and providing resistance is a friction or controlled resistance providing member having an aperture with a minimum inside dimension less than the outside diameter of the guide wire. A preferred friction providing member is a washer formed of a resilient material. One washer includes an aperture having a central hole and four radial slits. The central hole has an inside diameter less than the outside diameter of the guide wire to be received within the aperture. In a preferred embodiment, the washer is disposed at the proximal end of a tapered tube. The tube preferably decreases distally in outside diameter and hardness.

The four radial slits form four control flaps, which, in a relaxed state, form a minimum inside dimension less than the outside diameter of the guide wire. The four control flaps are biased so as to tend to reduce the minimum inside dimension of the aperture. Having received the guide wire, in a preferred embodiment, the four control flaps flex outward, bringing frictional force to bear on the received guide wire. The control flaps are typically arced outward about the guide wire, increasing the minimum inside dimension of the aperture. The arced control flaps typically also have a longitudinal component, extending outward, transverse to the plane of the washer.

In another embodiment, the aperture is formed by four radial slits having no central hole. In yet another embodiment, six radial slits form the aperture, again having no central hole. In still another embodiment, a single elongate slit forms the aperture. In an alternate embodiment, the aperture is formed by a hole in an elastic material, the hole having a relaxed state inside diameter less than the outside diameter of the guide wire to be received. The elastic material stretches radially upon receiving the guide wire, increasing the inside diameter of the hole in the stretched state.

In use, a guide wire typically has been disposed within a guide catheter, both of which have distal ends which have been positioned at a target site within a patient. The guide wire and guide catheter may have proximal ends which extend several inches from the entry site in the patient. A guide catheter exchange device according to the present invention is provided, having a controlled resistance aperture and preferably being about twice the length of the inserted guide catheter. The proximal end of the guide wire is threaded through the controlled resistance aperture. The distal end of the exchange device is advanced over the guide wire, within the guide catheter. The advancement continues until the controlled resistance aperture reaches the distal region of the guide wire.

With the distal region of the guide wire gripped by the controlled resistance aperture, the guide catheter can be retracted over both the guide wire and the exchange device shaft. The guide catheter, disposed over the guide wire for most of its length, exerts a proximal frictional force on the guide wire as the guide catheter is retracted. The controlled resistance aperture provides an amount of static friction sufficiently large to resist minor longitudinal forces tending to pull the guide wire proximally. The position of the exchange device can be maintained by holding a portion of the exchange device shaft as it extends proximally from the proximal end of the retracting guide catheter. When the guide catheter distal end has been retracted from the entry site, the guide wire and exchange device shafts can be held once again, near the entry site, and the guide catheter completely removed from the guide wire and exchange device shaft. A second guide catheter can then be threaded over the proximal end of the exchange device shaft and advanced over the exchange device shaft and guide wire. The second guide catheter can be advanced until the guide catheter distal region is disposed near the guide wire distal region.

BRIEF DESCRIPTION OF THE DRAWINGS

FIG. 1 is a fragmentary, longitudinal view of a guide catheter exchange device having a distal tube with a guide wire lumen drawn in phantom;

FIG. 2 is a fragmentary, longitudinal cross-sectional view of the tube proximal end of FIG. 1, having a proximal controlled resistance washer;

FIG. 3 is a perspective view of a controlled resistance washer suitable for use with the guide catheter exchange device of FIG. 1;

FIG. 4A is an end view of the controlled resistance washer of FIG. 3;

DETAILED DESCRIPTION OF THE PREFERRED EMBODIMENTS

Figure 4B:
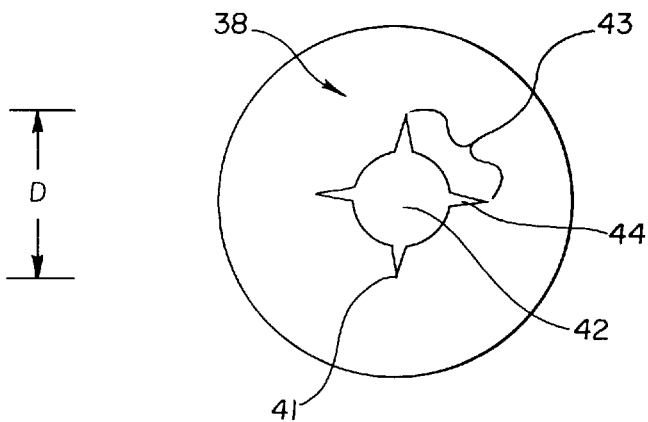
FIG. 4B is a detailed view of the guide wire aperture portion of FIG. 4A illustrating a central hole, radial slits and control flaps.

Referring now to FIG. 11 a guide catheter exchange device 20 is illustrated. Guide catheter exchange device 20 includes a distal region 24 and an elongate shaft 22 having a shaft distal region 36 and a tube or tubular sheath 26 disposed about shaft distal region 36. Tube 26 has a proximal end 32, a distal end 30, and a guide wire lumen 28 extending from proximal end 32 to distal end 30. In a preferred embodiment, tube proximal end 32 includes a controlled resistance washer 34. In one embodiment, controlled resistance washer 34 is located in an intermediate portion of tube 26. In yet another embodiment, washer 34 is located in a distal portion of tube 26. While preferred embodiments include tube 26, some embodiments have a controlled resistance washer with no tube. In a preferred embodiment, tube 26 is tapered distally, as illustrated in FIG. 1. The distal taper eases insertion of device 20 through a guide catheter and can ease retraction of the guide catheter over the tube distal end.

In a preferred embodiment, shaft 22 is formed of stainless steel, is about 70 to 90 inches in length, and has an outside diameter of about 0.021 inch. Tube 26 is preferably formed of polyether block amide and is about 6–15 inches in length. One embodiment tube is about 12 inches in length. Tube 26 is preferably formed of softer material in the tube distal portion. One embodiment tube 26 has a proximal region formed of 70–72D PEBAX, an intermediate transition region formed of 55–63D PEBAX, and a distal region formed of 40D PEBAX. The transition in materials can be formed utilizing an interrupted layer co-extrusion process, as for example, disclosed by Wang in U.S. Pat. No. 5,533, 985, the disclosure of which is incorporated herein by reference.

Referring now to FIG. 2, tube proximal end 32 is illustrated, having been cut away to illustrate guide wire lumen 28 and shaft distal region 36 within. Controlled resistance washer 34 is disposed at the proximal end of tube 26, having shaft 22 and a guide wire aperture 38 passing therethrough. Shaft 22 can be affixed to tube 26 with adhesive. Washer 34 is preferably affixed to tube 26 by heat bonding. Although washer 34 is shown affixed to the proximal end of tube 26, it is recognized that the washer 34 can be located anywhere along the length of tube 26, including the distal end 30.

Referring now to FIG. 3, controlled resistance washer 34 is illustrated in more detail, having width indicated at "W". The width or thickness of the washer varies across different embodiments, with the washer preferably abutting and affixed to the proximal end of tube 26. Controlled resistance washers according to the present invention can have guide wire apertures in differing sizes and geometries. Guide wire aperture 38 is illustrated in more detail in FIG. 4A. Aperture 38 includes a central hole 42 and radial slits 44 extending radially outward from central hole 42, thereby forming control flaps 43 between radial slits 44. Aperture 38 is illustrated in more detail in FIG. 4B. Radial slits 44 terminate radially in vertices 41. In the embodiment illustrated in FIG. 4B, the opposing walls of the radial slits do not touch one another, as material has been removed in forming the slit. Guide wires of various diameters can fit within guide wire aperture 38, with larger diameter guide wires causing control flaps to distend longitudinally more than small diameter guide wires.

In a preferred embodiment, central hole 42 has an outside diameter of about 0.008 inches and the vertex to vertex distance indicated by "D" in FIG. 4B is about 0.020 inches. A preferred outside diameter for washer 34 is about 0.050 inches. Washer 34 is preferably formed of a material such as a polyether block amide (PEBA); a urethane, a silicone or a cured urethane. Control flaps 43, formed of the same materials as the washer 34, when caused to flex by a guide wire protruding through aperture 38, retain a bias to close against the contained guide wire. The inward bias of control flaps 43 exerts frictional force against longitudinal movement of a guide wire disposed within aperture 38. The friction acts to inhibit longitudinal movement of a guide wire contained within aperture 38.

Washer 34, as illustrated in FIG. 3, includes an elongated shaft hole 40 to allow elongate shaft 22 to pass therethrough. This is necessary when washer 34 is mounted proximal to the distal end of elongate shaft 22. If the washer 34 is mounted within tube 26 distal of elongate shaft 22, hole 40 can be eliminated and the aperture 38 can be located anywhere on the washer 34, for example in the center portion, rather than offset near the outer edge.

Figure 5:
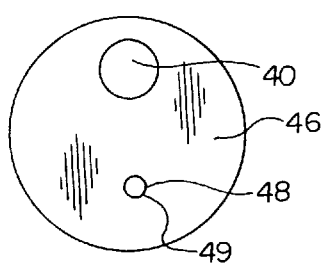
FIG. 5 is an end view of a controlled resistance washer having a central, undersized, elastic hole suitable for use in the guide catheter exchange device of FIG. 1.

Referring now to FIG. 5, another embodiment controlled resistance washer 46 is illustrated. A guide wire aperture 48 in the material of washer 46 has an aperture wall 49. Aperture 48 can deform radially and elastically to grip a guide wire within. While containing a guide wire having an outside diameter larger than the inside diameter of aperture 48, aperture 48 is enlarged to contain the guide wire. In a preferred embodiment, washer 46 is formed of an elastic material such as PEBA, urethane or silicone with a 25D durometer. In another embodiment, only the region near aperture walls 49 is elastic.

Figure 6:
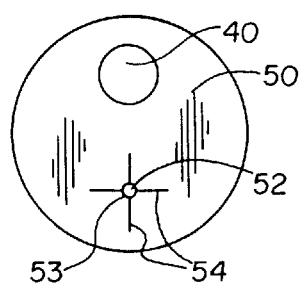
FIG. 6 is an end view of a controlled resistance washer having a central hole and radial slits suitable for use in the guide catheter exchange device of FIG. 1.

Referring now to FIG. 6, another embodiment controlled resistance washer 50 is illustrated. Washer 50 includes four radial slits and a central hole 52, thereby forming control flaps 53. Washer 50 can be formed by cutting radial slits 54 with a knife edge, the removing a central circle of material to form central hole 52. The amount of friction brought to bear on a guide wire can be adjusted by adjusting the inside diameter of central hole 52.

Figure 7:
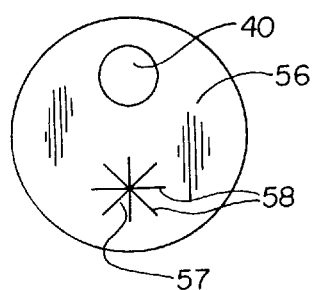
FIG. 7 is an end view of a controlled resistance washer having radial slits suitable for use in the guide catheter exchange device of FIG. 1.

Referring now to FIG. 7, yet another embodiment is illustrated in controlled resistance washer 56. Washer 56 includes radial slits 58 and control flaps 57, which can flex to admit and grip a guide wire inserted within. In washer 56, no material has been removed by the cuts for the radial slits.

Figure 8:
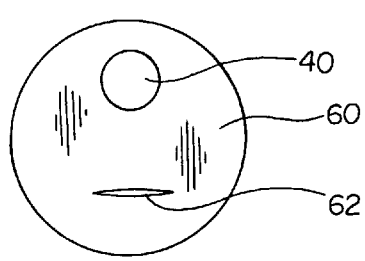
FIG. 8 is an end view of a controlled resistance washer having a single slit, suitable for use in the guide catheter exchange device of FIG. 1.

Referring now to FIG. 8, still another embodiment is illustrated by washer 60, which includes a slit 62 for admitting a guide wire. Slit 62 can be formed by removing material within the slit. The width of slit 62 is greater in the center than at the edges. In another embodiment, a slit is formed having no width.

The present invention may be used where a guide catheter exchange is desired without dislodging the distal end of a guide wire disposed within the guide catheter. A guide catheter proximal end extends proximally from a patient and a guide wire proximal end may extend proximally from the guide catheter. A guide catheter exchange device as previously described is provided, preferably having a tube disposed on the distal end of an elongate shaft, with a controlled resistance washer disposed near the proximal region of the tube. The exchange device shaft is preferably about twice the length of the guide catheter disposed within the patient.

The guide wire proximal end can be threaded through the tube distal guide wire port, through the tube and through the guide wire aperture in the controlled resistance washer. The proximal end of the guide wire is then held while the guide catheter exchange device is advanced distally into the patient over the guide wire, within the guide catheter. The friction between washer and guide wire is countered by firmly gripping the guide wire proximal end, preventing the guide wire distal end from being advanced distally into the patient. With the aid of fluoroscopic visualization, the position of the guide catheter exchange device can be monitored, and advancement preferably stopped when the exchange device tube distal end has been advanced over the guide wire distal end.

With the exchange device tubular sheath disposed over the guide wire distal end, the original guide catheter can be retracted over the guide wire and exchange device elongate shaft. The guide catheter, as it is being retracted, exerts a friction force over substantially the entire guide wire length. This friction force is counteracted by the friction of the exchange device controlled resistance washer acting upon the guide wire. The static friction between the exchange device and guide wire should be higher than the static friction between the retracting guide catheter and guide wire within.

The guide catheter can be retracted until the distal end of the guide catheter has been withdrawn from the patient's body, exposing a length of exchange device shaft extending proximally out of the patient's body and distally out of the guide catheter. This portion of exchange device shaft can then be firmly grasped, and the guide catheter slid over the exchange device proximal end.

A new guide catheter can then be advanced over the shaft of the exchange device and over the guide wire. The advancing guide catheter exerts some frictional force on the guide wire contained within. Guide wire distal movement is inhibited by the frictional force provided by the exchange device, which can be firmly held at the proximal end by the treating physician. The new guide catheter can be advanced until it is positioned near the position of the previous guide catheter. With the new guide catheter in place, the exchange device can be retracted proximally over the guide wire. The reason the controlled resistance washer gripping the guide wire does not cause the guide wire to retract along with the retracting exchange device is that the washer applies a friction force to the guide wire and the operator manually restrains movement of the guide catheter exchange device.

Numerous advantages of the invention covered by this document have been set forth in the foregoing description. It will be understood, however, that this disclosure is, in many respects, only illustrative. Changes may be made in details, particularly in matters of shape, size, and arrangement of parts without exceeding the scope of the invention. The inventions's scope is, of course, defined in the language in which the appended claims are expressed.

What is claimed is:

1. A guide catheter exchange device comprising:
   an elongate member having a distal region; and
   means for receiving a guide wire and providing resistance to longitudinal movement of said guide wire, said receiving and resistance means operably connected to said elongate member distal region and including a guide wire receiving portal that has a relaxed inside dimension that is less than an outside dimension of said guide wire such that the guide wire receiving portal frictionally engages at least a portion of said guide wire when said guide wire is inserted therein.

2. A method for retracting a guide catheter having a proximal end and a distal end disposed over a guide wire having a distal end disposed within the body of a patient comprising the steps:
   providing a guide catheter exchange device including a distal end,
      an elongate member having a proximal end and a distal region, said elongate member being sufficiently long such that said proximal end extends from said guide catheter proximal end when said guide catheter distal end is retracted from, and proximate to, said patient's body, and
      means for receiving a guide wire and providing resistance to longitudinal movement of said guide wire, said receiving and resistance means operably connected to said elongate member distal region;
   inserting said guide wire proximal end into said exchange device receiving and resistance means;
   inserting said exchange device distal end into said guide catheter proximal end;
   advancing said exchange device distally over said guide wire within said guide catheter until said exchange device distal end is proximate said guide wire distal end;
   retracting said guide catheter proximally over said exchange device and over said guide wire while substantially maintaining the positions of said exchange device and said guide wire; and
   continuing said retracting until said guide catheter distal end is retracted from said patient, exposing a portion of said guide wire and exchange device.

3. A method for retracting a guide catheter as recited in claim 2 further comprising grasping said exposed guide wire portion and further retracting said guide catheter.

4. A method for retracting a guide catheter as recited in claim 2 further comprising grasping said exposed exchange device portion and further retracting said guide catheter.

5. A method for advancing a guide catheter having a proximal end and a distal end over a guide wire, the guide wire having a proximal end and a distal end, the distal end being disposed within the body of a patient comprising the steps:

provinding a guide catheter exchange device including
a distal end,
an elongate member having a proximal end and a distal region, said elongate member being sufficiently long such that said proximal end extends from said guide catheter proximal end when said guide catheter distal end is retracted from, and proximate to, said patient's body, and
means for receiving a guide wire and providing resistance to longitudinal movement of said guide wire, said receiving and resistance means operably connected to said elongate member distal region;
inserting said guide wire proximal end into said exchange device receiving and resistance means;
advancing said exchange device distally over said guide wire until said exchange device distal end is proximate said guide wire distal end;
inserting said guide catheter distal end over said exchange device proximal end;
advancing said guide catheter distal end over said exchange device shaft;
inserting said guide catheter distal end over said guide wire proximal end;
advancing said guide catheter distal end over said guide wire; and
advancing said guide catheter distally over said exchange device shaft and over said guide wire while substantially maintaining the positions of said exchange device and said guide wire.

6. A guide wire stabilization device for resisting longitudinal movement of a guide wire having an outside diameter comprising:

an elongate member having a longitudinal axis, a proximal end and a distal region; and
a friction providing member including an aperture therethrough operably connected to said elongate shaft distal region, said aperture adapted to receive said guide wire, said aperture having a relaxed state with a minimum inside dimension less than the outside diameter of said guide wire, such that said aperture provides frictional resistance to longitudinal movement of said guide wire.

7. A guide wire stabilization device as recited in claim 6, wherein said friction providing member aperture includes walls formed of an elastomeric material, such that friction is provided by substantially elastic radial stretching increasing said aperture minimum inside dimension to receive said guide wire.

8. A guide wire stabilization device as recited in claim 6, wherein said aperture is formed within a resilient material and has a center, wherein said aperture includes at least one slit extending radially outward from said aperture center, said slit creating a flap on either side, such that friction is provided by a radially inward bias of said flaps against said inserted guide wire.

9. A guide wire stabilization device as recited in claim 8, wherein said aperture has a central hole at said center and said slits extend radially outward from said central hole.

10. A guide wire stabilization device as recited in claim 9, wherein said slits have a width, said width decreasing with radial distance from said central hole.

11. A guide wire stabilization device as recited in claim 6, further comprising a tubular member having a lumen therethrough in communication with said friction providing member aperture.

12. A guide wire stabilization device as recited in claim 11, wherein said tubular member includes a proximal portion and said friction providing device is located in said tubular member proximal portion.

13. A guide wire stabilization device as recited in claim 12, wherein said tubular member has a distally tapering outside diameter.

14. A guide wire stabilization device for resisting longitudinal movement of a guide wire having an outside diameter comprising:

an elongate member having a longitudinal axis, a proximal end and a distal region;
a tubular member operably connected to said elongate shaft distal region, said tubular member having a proximal region and lumen therethrough; and
a washer formed of resilient material including an aperture therethrough, said washer operably connected to said tubular member proximal region, said aperture adapted to receive said guide wire, said aperture having a relaxed state with a minimum inside dimension less than the outside diameter of said guide wire, such that said aperture provides frictional resistance to longitudinal movement of said guide wire.

15. A guide wire stabilization device as recited in claim 14, wherein said aperture has at least one slit, said slit forming a flap on either side.

16. A guide wire stabilization device as recited in claim 14, wherein said aperture has a center and at least one slit, said slit extending radially outward from said center.

* * * * *